United States Patent [19]

Hase et al.

[11] 4,057,623

[45] Nov. 8, 1977

[54] COSMETIC EMULSIONS CONTAINING N-VINYLPYRROLIDONE-ALKYL ACRYLATE COPOLYMERS

[75] Inventors: Brigitte Hase, Erkrath; Joachim Galinke, Langenfeld; Bernd Wegemund, Haan, all of Germany

[73] Assignee: Henkel Kommanditgesellschaft auf Aktien, Dusseldorf, Germany

[21] Appl. No.: 670,381

[22] Filed: Mar. 25, 1976

[30] Foreign Application Priority Data

Mar. 29, 1975 Germany .............................. 2514100

[51] Int. Cl.$^2$ .............................................. A61K 31/74
[52] U.S. Cl. ............................... 424/78; 424/DIG. 2; 424/168
[58] Field of Search .................... 424/78, 168, DIG. 2

[56] References Cited

U.S. PATENT DOCUMENTS

| 3,914,403 | 10/1975 | Valan | 424/78 |
| 3,954,960 | 5/1976 | Valan | 424/358 |

FOREIGN PATENT DOCUMENTS

| 1,931,080 | 12/1970 | Germany | 424/78 |

*Primary Examiner*—Dale R. Ore
*Attorney, Agent, or Firm*—Hammond & Littell

[57] ABSTRACT

Water-in-oil emulsions wherein the emulsifier consists essentially of a copolymer or terpolymer of N-vinylpyrrolidone with a $C_{6-24}$ alkyl or cycloalkyl acrylate or methacrylate, and vinyl acetate if desired, and the continuous phase is a cosmetically acceptable oily material which can be prepared easily, safely and inexpensively. The emulsions are substantially odorless and are cosmetically acceptable for the care of the skin.

9 Claims, No Drawings

COSMETIC EMULSIONS CONTAINING N-VINYLPYRROLIDONE-ALKYL ACRYLATE COPOLYMERS

Field of Invention

The invention relates to cosmetic emulsions of the water-in-oil type having a content of polymers of N-vinylpyrrolidone with alkyl acrylate and/or methacrylate esters and if desired vinyl acetate as emulsifiers and stabilizers. The invention includes the emulsions themselves and methods for their preparation.

RELATED ART

In contrast to the production of oil-in-water emulsions, only a limited number of emulsifying agents are available, the best of which are becoming increasingly scarce, for producing cosmetic emulsions of the water-in-oil type. Wool fat and its derivatives are still some of the most important emulsifying agents for producing creams of the water-in-oil type. However, despite their uncontested advantages, wool fat and its derivatives such as lanolin have certain disadvantages. Thus, conventional water-in-oil emulsifying agents based on wool fat and its derivatives impart a strong intrinsic odor to creams which contain them. This, in turn, requires strong perfuming which frequently cannot be tolerated by persons with sensitive skin. However, this influencing of the quality of the cream by a strong intrinsic odor is not only peculiar to wool fat and its derivatives, but also extends to lanolin-free water-in-oil emulsifying agents based on animal sterols, particularly those based on cholesterol. Furthermore, low molecular weight emulsifying agents, together with the effective substances of the cream, can be absorbed by the skin, which is not desirable in all cases.

The most widely known water-in-oil emulsifying agents for cosmetic purposes include, in addition to the said emulsifying agents based on wool fat, wax alcohols and sterols, and the oleic acid esters of various polyols, such as glycerine, pentaerythritol, trimethylolpropane and sorbitol. However, due to the unsaturated character of their acid component, the oleic acid esters have various disadvantages with respect to their technical use, so that there is a genuine need for new and suitable water-in-oil emulsifying agents.

OBJECTS OF THE INVENTION

One object of the present invention is the development of a cosmetic emulsion or cream of the water-in-oil type which can be prepared easily and safely from inexpensive materials without need for costly emulsifying equipment.

Another object of the invention is the development of a cosmetic emulsion of the above type which is substantially odorless and which, therefore, can find general acceptance when containing only a small and harmless amount of perfume.

A further object of the invention is the development of such an emulsion which is stable at an acid, neutral and alkaline pH.

A particular object of the present invention is the production of a cosmetic emulsion of the water-in-oil type consisting essentially of (1) from 2% to 20% by weight of a polymeric emulsifier capable of forming water-in-oil creams consisting of a copolymer of (a) N-vinylpyrrolidone, (b) acrylates of the formula:

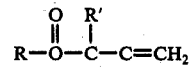

wherein R is a member having from 6 to 24 carbon atoms selected from the group consisting of alkyl, alkenyl, cycloalkyl and alkylcycloalkyl, and R' is a member selected from the group consisting of hydrogen and methyl, and (c) vinyl acetate wherein the molar ratios of [(a)+(c)]: (b) are from 1:1 to 1:20 and the molar ratios of (c): (a) are 0:1 to 3:1, (2) from 20% to 75% by weight of water and (3) the remainder to 100% by weight of a cosmetically acceptable oily material.

These and other objects of the present invention will become more apparent as the description thereof proceeds.

DESCRIPTION OF THE INVENTION

It has now been discovered that the objections of the prior art emulsifiers have been overcome and the above objects have been achieved by the discovery of cosmetic emulsions of the water-in-oil type having a content of a copolymer or terpolymer from N-vinylpyrrolidone, a (meth)acrylate having 6 to 24 carbon atoms in the ester component thereby and, if required, vinyl acetate, in a quantity of from 2% to 20% by weight, a quantity of from 20% to 75% by weight of water, relative to the total emulsion, and vegetable or animal fats, waxes, fatty alcohols, hydrocarbons and further auxiliary substances normally used in cosmetic emulsions.

More particularly, the present invention relates to a cosmetic emulsion of the water-in-oil type consisting essentially of (1) from 2% to 20% by weight of a polymeric emulsifier capable of forming water-in-oil creams consisting of a copolymer of (a) N-vinylpyrrolidone, (b) acrylates of the formula:

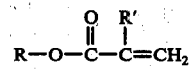

wherein R is a member having from 6 to 24 carbon atoms selected from the group consisting of alkyl, alkenyl, cycloalkyl and alkylcycloalkyl, and R' is a member selected from the group consisting of alkyl, alkenyl, cycloalkyl and alkylcycloalkyl, and r' is a member selected from the group consisting of hydrogen and methyl, and (c) vinly acetate wherein the molar ratios of [(a)+(c)]:(b) are from 1:1 to 1:20 and the molar ratios of (c):(a) are 0:1 to 3:1, (2) from 2% to 75% by weight of water, and (3) the remainder to 100% by weight of a cosmetically acceptable oily material.

The copolymers or terpolymers from N-vinylpyrrolidone, the (meth)acrylates and, if required, vinyl acetate, usuable as emulsifying agents in the cosmetic emulsions in accordance with the invention, can be produced in a generally known manner by one processing step under the normal conditions of free radical polymerization. Polymerization can be carried out in non-polar solvents., such as benzene or toluene, or in polar solvents, such as methanol or tetrahydrofurane, by means of peroxides, such as dibenzoyl peroxide or lauroyl peroxide, and azo compounds, such as azobisisobutyronitrile as free-radical polymerization catalysts.

The technical production is effected to best advantage in the form of solution polymerization in such solvents which only dissolve the monomers but not the polymers produced (precipitation polymerization), especially since polymers are produced which are satisfactorily precipitable and which are virtually free from monomers (J. Scheiber, Chemie und Technologie der Kuenstlichen Harze, Vol. I, pages 362 ff., 1961).

Monomeric starting compounds of the polymeric emulsifier which may be mentioned in addition to N-vinylpyrrolidone and, if required, vinyl acetate, are, for example:

hexyl acrylate
octyl acrylate
2-ethylhexyl acrylate
nonyl acrylate
decyl acrylate
lauryl acrylate
myristyl acrylate
cetyl acrylate
stearyl acrylate
oleyl acrylate
behenyl acrylate
tert. butylcyclohexyl acrylate
hexyl methacrylate
octyl methacrylate
nonyl methacrylate
decyl methacrylate
lauryl methacrylate
myristyl methacrylate
cetyl methacrylate
stearyl methacrylate
oleyl methacrylate
behenyl methacrylate, etc.

Particular importance is attached to the acrylic or methacrylic acid esters of the fatty alcohols having 8 to 14 carbon atoms, such as octyl acrylate, nonyl acrylate, decyl acrylate, lauryl acrylate, myristyl acrylate, octyl methacrylate, nonyl methacrylate, decyl methacrylate, lauryl methacrylate, and myristyl methacrylate.

In the copolymers or terpolymers usable in accordance with the invention, the molar ratios of the monomers N-vinylpyrrolidone + (vinyl acetate): the (meth-)acrylate are 1:1 to 1:20, preferably 1:1.5 to 1:10, wherein the molar ratios of vinyl acetate:N-vinylpyrrolidone are 0:1 to 3:1.

The copolymers or terpolymers usable in accordance with the invention have average molecular weights between 2,000 and 100,000. Those having average molecular weights between 3,000 and 20,000 are particularly suitable in view of the easy processability and the quality of the emulsions obtained. Polymers having molecular weights within this range can be prepared in known manner by adjusting the amount of catalyst, the nature and amount of the solvent, and by adding polymerization or molecular weight regulators.

The emulsions in accordance with the invention are manufactured in a simple and known manner by dissolving the copolymers or terpolymers, acting as emulsifying agents, in the oily phase at an increased temperature of approximately 60° to 70° C. Subsequently the desired quantity of water heated to approximately 60° to 65° C is added, and the emulsion obtained is stirred while cooling. Further constituents of the cosmetic emulsions to be manufactured, such as skin moisture regulators, vegetable extracts of effective substances, vitamins, hormones, pigments, salts, perfume oil, UV filtering media, dyestuffs, etc., are advantageously dissolved or distributed in the phase which absorbs these substances to best advantage. The required quantity of emulsifying agent is 2% to 20% by weight, preferably 5% to 10% by weight, relative to the total cosmetic emulsion. The amount of water to be incorporated can be 20% to 75% by weight, preferably 45% to 65% by weight, relative to the total cosmetic emulsion.

Products conventionally used, such as animal and vegetable oils and fats, synthetic esters of higher fatty acids with alkanols, higher fatty alcohols, waxes, so-called mineral fats and oils, such as paraffin oil, "Vaseline" ®, ceresine, silicone oils and silicone fats are suitable as the oily phase of the cosmetic emulsions in accordance with the invention. They should have melting points above 30° C and be substantially solid at room temperature. The oily phase represents the remainer of the weight of the total cosmetic emulsion.

German Offenlegungsschrift (DOS) No. 2,116,787 has already described the use of water-in-oil emulsifying agents in the form of sequence polymers which have at the same time at least one lipophilic sequence and one hydrophilic sequence. Each of the sequences should have the properties of the corresponding homopolymers. These sequence polymers are obtained by anionic polymerization which places high demands on the purity of the substances used, and requires working at low temperatures under protective gas and increased safety precautions when handling spontaneously inflammable catalysts. In contrast to this, the emulsifying agents required for producing the emulsions in accordance with the present invention can be manufactured in a simple manner.

In accordance with the German Offenlegungsschrift (DOS) No. 1,745,216, copolymers comprising a monomer having a lipophilic chain and a monomer having a carboxylic acid anhydride function are proposed as emulsifying agents for water-in-oil emulsions. However, such products are sensitive to hydrolysis and, to avoid this disadvantage, a further processing step in addition to polymerization is necessary in order to convert them into a more stable form.

In general, the emulsions in accordance with the present invention can also be used by persons having a sensitive skin. Since they do not have any appreciable intrinsic odor, they do not require heavy perfuming which, in turn, has an advantageous effect upon the compatibility and also saves costs.

Furthermore, the emulsions in accordance with the invention are distinguished by a low sensitivity to acid, thus rendering it possible to incorporate acidic raw materials therein, such as organic acids. A further very advantageous property of the emulsions in accordance with the invention is their high resistance to temperature, which enables them to withstand a thermal stress of 50° C for a period of 6 weeks without any detrimental effects.

The following examples are intended to further explain the invention, but without limiting the invention to these examples.

EXAMPLES

The following illustrates the production of a copolymer which may be used in cosmetic emulsions of the invention.

EXAMPLE 1

N-Vinylpyrrolidone/lauryl acrylate copolymer (1:2.5 molar ratio)

A reaction mixture was prepared by dissolving 22.2 gm (0.2 mol) of N-vinylpyrrolidone and 119.5 gm (0.5 mol) of lauryl acrylate in 330 gm of toluene and adding 2.8 gm of dibenzoyl peroxide as catalyst. The reaction mixture was agitated for 6 hours at 80° C. After the reaction had been completed, the solvent was distilled off and the polymer was washed a few times with methanol. 133 gm (95% of theory) of N-vinylpyrrolidone/lauryl acrylate copolymer (1:2.5) were obtained.

The other copolymers used in the examples given below were obtained in an analogous manner.

EXAMPLE 2

Cosmetic emulsion based on Vaseline ®

A mixture of 10 gm of N-vinylpyrrolidone/lauryl acrylate copolymer (1:2.5 molar ratio) and 40 gm of Vaseline ® was melted together by heating to 65° C. 50 gm of water at 65° C were added to the melt, and the mixture was stirred. A water-in-oil emulsion formed which was allowed to cool with continued agitation. The emulsion can be readily produced by manual stirring. The cream obtained was stable for several months and did not exhibit any change even after 6 weeks of storage at 50° C. This basic cream can be used to produce various skin creams by further adding various effective substances and perfume oils.

By way of example, the following copolymers can be used with the same satisfactory results instead of the N-vinylpyrrolidone/lauryl acrylate copolymer (1:2.5 molar ratio):

| Copolymer | Molar ratio |
|---|---|
| N-vinylpyrrolidone/lauryl acrylate | (1:1.5) |
| N-vinylpyrrolidone/nonyl methacrylate | (1:15) |
| N-vinylpyrrolidone/octyl acrylate | (1:20) |
| N-vinylpyrrolidone/decyl methacrylate | (1:8) |
| N-vinylpyrrolidone/decyl acrylate | (1:10) |
| N-vinylpyrrolidone/myristyl methacrylate | (1:4) |
| N-vinylpyrrolidone/myristyl acrylate | (1:6) |
| N-vinylpyrrolidone/lauryl methacrylate | (1:7) |
| N-vinylpyrrolidone/cetyl acrylate | (1:5) |
| N-vinylpyrrolidone/stearyl methacrylate | (1:2) |
| N-vinylpyrrolidone/2-ethylhexyl acrylate | (1:10) |

EXAMPLE 3

Cosmetic emulsion based on hardened peanut oil/decyl oleate mixture

A mixture of 4 gm of N-vinylpyrrolidone/decyl acrylate copolymer (1:6 molar ratio), 40 gm of a hardened peanut oil/decyl oleate mixture (90:10 by weight), 3 gm of beeswax, and 3 gm of glyceryl monooleate was melted at 70° C. 50 gm of water at 65° C were added thereto with continuous agitation, and the mixture was allowed to cool with continued agitation. A cream was obtained, the stability properties of which were largely similar to those of the cream of Example 2.

Various skin creams based on this basic cream can be produced by incorporating further effective substances, such as skin moisture regulators (moisturizing agents), vegetable extracts, and perfume oils.

By way of example, the following copolymers can be used with the same satisfactory results instead of the N-vinylpyrrolidine/decyl acrylate copolymer (1:6):

| Copolymer | Molar ratio |
|---|---|
| N-vinylpyrrolidone/myristyl methacrylate | (1:3) |
| N-vinylpyrrolidone/decyl methacrylate | (1:5) |
| N-vinylpyrrolidone/lauryl acrylate | (1:8) |
| N-vinylpyrrlidone/cetyl methacrylate | (1:4) |
| N-vinylpyrrolidone/behenyl acrylate | (1:2) |
| N-vinylpyrrlidone/decyl methacrylate | (1:6) |
| N-vinylpyrrolidone/octyl acrylate | (1:10) |
| Nvinylpyrrlidone/tert. butyl cyclohexyl acrylate | (1:8) |

EXAMPLE 4

Cosmetic emulsions based on Vaseline ®/decyl oleate mixture

A mixture of 7 gm of N-vinylpyrrolidone/vinyl acetate/lauryl myristyl acrylate polymer (molar ratio 2:1:6), 10 gm of Vaseline ®, 15 gm of decyl oleate, 3 gm of beeswax and 2 gm of calcium stearate was melted together by heating to 65° C. 63 gm of water at 65° C were stirred into this mixture and agitation was continued until an emulsion was obtained. The mixture was cooled to room temperature with continued stirring. The product was a cream, the stability properties of which were similar to those of the two creams described above.

A large number of cosmetic creams based on this basic cream can be produced by incorporating cosmetically effective amounts of cosmetically effective substances and perfume oils therein.

By way of example, the following polymers can be used with the same satisfactory results instead of the N-vinylpyrrolidone/vinyl acetate/lauryl myristyl acrylate polymer (2:1:6 molar ratio):

| | Molar ratio |
|---|---|
| N-vinylpyrrolidone/vinyl acetate/lauryl acrylate | (3:1:12) |
| N-vinylpyrrolidone/vinyl acetate/myristyl methacrylate | (2:1:6) |
| N-vinylpyrrolidone/vinyl acetate/octyl methacrylate | (2:1:15) |
| N-vinylpyrrolidone/vinyl acetate/decyl acrylate | (1:1:12) |
| N-vinylpyrrlidone/vinyl acetate/lauryl acrylate | (1:1:10) |
| N-vinylpyrrolidone/vinyl acetate/stearylacrylate | (2:1:6) |
| N-vinylpyrrolidone/vinyl acetate/myristyl acrylate | (1:2:10) |
| N-vinylpyrrolidone/vinyl acetate/lauryl methacrylate | (1:3:8) |

EXAMPLE 5

Cosmetic emulsions based on hardened peanut oil

A mixture of 6 gm of N-vinylpyrrolidone/vinyl acetate/octyl-decyl acrylate polymer (1:1:20 molar ratio) and 44 gm of hardened peanut oil was melted together by heating to 65° C. 50 gm of water at 65° C were stirred into this mixture, and the mixture was cooled with continued agitation. The product was a cream, the stability properties of which were largely similar to those of the previously mentioned creams.

The cream can act as a basic cream for various cosmetic preparations.

By way of example, the following polymers can be used with the same satisfactory results instead of the N-vinylpyrrolidone/vinyl acetate/octyl-decyl acrylate polymer (1:1:20 molar ratio) used above:

|  | Molar ratio |
| --- | --- |
| N-vinylpyrrolidone/vinyl acetate/ lauryl myristyl acrylate | (1:2:10) |
| N-vinylpyrrolidone/vinyl acetate/ lauryl methacrylate | (1:3:8) |
| N-vinylpyrrolidone/vinyl acetate/ decyl methacrylate | (2:1:6) |
| N-vinylpyrrolidone/vinyl acetate/ myristyl acrylate | (1:2:10) |
| N-vinylpyrrolidone/vinyl acetate/ lauryl acrylate | (3:1:12) |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A cosmetic emulsion of the water-in-oil type consisting essentially of (1) from 2% to 20% by weight of a polymeric emulsifier capable of forming water-in-oil creams consisting essentially of a copolymer of (a) N-vinylpyrrolidone and (b) acrylates of the formula:

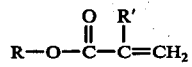

wherein R is a member having from 6 to 24 carbon atoms selected from the group consisting of alkyl, alkenyl, cycloalkyl and alkylcycloalkyl, and R' is a member selected from the group consisting of hydrogen and methyl, and (c) vinyl acetate wherein the molar ratios of [(a)+(c)]:(b) are from 1:1 to 1:20 and the molar ratios of (c):(a) are 0:1 to 3:1, (2) from 20% to 75% by weight of water and (3) the remainder to 100% by weight of a cosmetically acceptable oily material.

2. The cosmetic emulsion of claim 1 wherein said cosmetically acceptable oily material has a melting point above 30° C and is selected from the group consisting of vegetable fat, animal fat, wax, higher fatty alcohols, mineral oil and silicone oil.

3. The cosmetic emulsion of claim 1 wherein said polymeric emulsifier is present in an amount of from 5% to 10% by weight and said water is present in an amount of from 45% to 65% by weight.

4. The cosmetic emulsion of claim 1 wherein R is alkyl having from 8 to 14 carbon atoms.

5. An emulsion of claim 1 wherein the molar ratio of (a)+(c):(b) is from 1:1.5 to 1:10.

6. An emulsion of claim 1 wherein said polymeric emulsifier has an average molecular weight of from 2,000 to 100,000.

7. An emulsion of claim 1 wherein said average molecular weight is from 3,000 to 20,000.

8. An emulsion according to claim 1 wherein the emulsifier is a 1:2.5 molar ratio N-vinylpyrrolidone/lauryl acrylate copolymer.

9. In the method for the production of a cosmetic emulsion of the water-in-oil type comprising mixing an emulsifier capable of forming water-in-oil creams with a cosmetically acceptable oily material in the liquid phase at elevated temperatures, mixing therewith from 20% to 75% by weight of water, cooling under agitation and recovering said cosmetic emulsion of the water-in-oil type, the improvement consisting of adding from 2% to 20% by weight of a copolymer of (a) N-vinylpyrrolidone, (b) acrylates of the formula

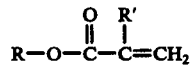

wherein R is a member having from 6 to 24 carbon atoms selected from the group consisting of alkyl, alkenyl, cycloalkyl and alkylcycloalkyl, and R' is a member selected from the group consisting of hydrogen and methyl, and (c) vinyl acetate wherein the molar ratios of [(a)+(c)]:(b) are from 1:1 to 1:20 and the molar ratios of (c):(a) are 0:1 to 3:1, (2) from 20% to 75% by weight of water and (3) the remainder to 100% by weight of a cosmetically acceptable oily material, as said emulsifier.

* * * * *